US011246853B2

(12) United States Patent
Cattuzzato et al.

(10) Patent No.: US 11,246,853 B2
(45) Date of Patent: Feb. 15, 2022

(54) METHOD FOR EVALUATING THE ABILITY OF A COMPOSITION TO PREVENT MUSCLE DAMAGE AND FATIGUE; FOOD SUPPLEMENT AND DRUG

(71) Applicant: SOCIETE D'EXPLOITATION DE PRODUITS POUR LES INDUSTRIES CHIMIQUES SEPPIC, Paris (FR)

(72) Inventors: Laetitia Cattuzzato, Castres (FR); Catherine Kern, Castres (FR); Ambre De Pooter, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 16/097,416

(22) PCT Filed: Mar. 8, 2017

(86) PCT No.: PCT/FR2017/050508
§ 371 (c)(1),
(2) Date: Oct. 29, 2018

(87) PCT Pub. No.: WO2017/187033
PCT Pub. Date: Nov. 2, 2017

(65) Prior Publication Data
US 2019/0160042 A1    May 30, 2019

(30) Foreign Application Priority Data
Apr. 27, 2016 (FR) ........................ 1653737

(51) Int. Cl.
*A61K 31/355* (2006.01)
*A23L 33/15* (2016.01)
*A23L 33/165* (2016.01)
*A61K 31/366* (2006.01)
*G01N 33/50* (2006.01)
*A23L 33/10* (2016.01)
*A61K 45/06* (2006.01)
*A23L 33/105* (2016.01)
*A23L 33/16* (2016.01)
*A61P 39/00* (2006.01)
*A61P 3/00* (2006.01)

(52) U.S. Cl.
CPC ............ *A61K 31/355* (2013.01); *A23L 33/10* (2016.08); *A23L 33/105* (2016.08); *A23L 33/15* (2016.08); *A23L 33/16* (2016.08); *A23L 33/165* (2016.08); *A61K 31/366* (2013.01); *A61K 45/06* (2013.01); *A61P 3/00* (2018.01); *A61P 39/00* (2018.01); *G01N 33/5061* (2013.01); *A23V 2002/00* (2013.01); *G01N 2333/5412* (2013.01); *G01N 2333/9123* (2013.01); *G01N 2800/10* (2013.01)

(58) Field of Classification Search
None
See application file for complete search history.

(56) References Cited

U.S. PATENT DOCUMENTS

| 6,054,128 A * | 4/2000 | Wakat ............... A23L 33/10 424/439 |
| 6,451,341 B1 * | 9/2002 | Slaga ............... A61K 38/43 424/468 |
| 2016/0082055 A1 * | 3/2016 | Latge ............... C08L 77/02 424/93.45 |

FOREIGN PATENT DOCUMENTS

| DE | 200 12 510 U1 | 11/2000 |
| ZA | 200300639 B | 8/2003 |

OTHER PUBLICATIONS

Kawashima, Motoko; et al; "Dietary Supplementation with a Combination of Lactoferrin, Fish Oil,and Enterococcus faecium WB2000 for Treating Dry Eye: A Rat Model and Human Clinical Study" The Ocular Surface, 14, 255-263, 2016 (Year: 2016).*
International Search Report, dated Oct. 5, 2017, from corresponding PCT Application No. PCT/FR2017/050508.
Office Action issued in Korean Patent Application No. 10-2018-7032984 dated May 12, 2021.
Hurst et al., "Blueberry fruit polyphenolics suppress oxidative stress-induced skeletal muscle cell damage in vitro," Molecular Nutrition & Food Research, vol. 54, No. 3, Mar. 1, 2010, pp. 353-363, XP055328120.
Owens et al., "Characterization of primary human skeletal muscle cells from multiple commercial sources", In Vitro Cellular & Developmental Biology, Animal, vol. 49, No. 9, Jul. 17, 2013, pp. 695-705, XP055328210.

(Continued)

*Primary Examiner* — David W Berke-Schlessel
(74) *Attorney, Agent, or Firm* — Nixon & Vanderhye

(57) ABSTRACT

Disclosed is a method for evaluating the ability of a chemical substance or a chemical composition to prevent muscle fatigue and damage induced by physical exertion in humans; edible composition including at least one salt of a multivalent metal cation, at least one compound selected between vitamin E or vitamin E acetate, at least one edible polyphenol compound selected from compounds of the flavonol family, compounds of the anthocyanin family, compounds of the phenolic acid family and compounds of the flavonol family and/or the glucosylated derivatives thereof, in which the molar ratio/is of at least 0.50 and not more than 2.00; its use as a food supplement or for preparing a food supplement composition or as a drug for preventing muscle fatigue and/or muscle damage induced by physical exertion, in a method for the treatment of the human body by therapy.

5 Claims, No Drawings

(56) References Cited

OTHER PUBLICATIONS

Finsterer, "Biomarkers of peripheral muscle fatigue during exercise", BMC Musculoskeletal Disorders, vol. 13, No. 218, Nov. 8, 2012, 13 pages, XP021135740.
Nikolic et al., "Electrical Pulse Stimulation of Cultured Human Skeletal Muscle Cells as an In Vitro Model of Exercise," PLOS one, vol. 7, No. 3, Mar. 22, 2012, 10 pages, XP055328129.
Anonymous, "VITILICAPS," 2013, XP055408372, Retrieved from the Internet: URL:http://www.lyconcepts.com/vitilicaps, retrieved on Sep. 20, 2017, 2 pages.
Anonymous, "Fall/Winter Issue 2013, Support Heart Health With Omega Oils! p. 38 Join the BIOVEA Community on FACEBOOK! Strengthen and Improve Your Skin Simple Ways To Products Designed Specifically To Keep You Slim and Fit! Fitness Section!", Biovea, No. Fall/Winter, Jan. 1, 2013, 99 p. XP055408548.
De Pooter et al., "In vitro protective effect of the association of wine polyphenols, vitamin E and zinc on muscle Fatigue and damages induced by physical exercise," Jun. 29, 2016 (Jun. 29, 2016), XP055367850, 3 pages, exact document as issued by EPO on Oct. 5, 2017.
Anonymous, "Journal of ISANH vol. 3: Special Issue for Porto Polyphenols 2016," Journal of ISANH, Jun. 29, 2016, XP055369257, 1 page, exact document as issued by EPO on Oct. 5, 2017.
Covington et al., "Myokine Expression in Muscle and Myotubes in Response to Exercise Stimulation," Medicine & Science in Sports & Exercise, Mar. 2016, vol. 48, No. 3, pp. 384-390.
Allen, "Skeletal Muscle Function: Role of Ionic Changes in Fatigue, Damage and Disease," Clinical and Experimental Pharmacology and Physiology, 2004, pp. 485-493.
Allen et al., "Mechanisms of stretch-induced muscle damage in normal and dystrophic muscle: role of ionic changes," The Physiological Society, 2005, pp. 723-735.
Allen et al., "Skeletal Muscle Fatigue: Cellular Mechanisms," American Physiological Society, 2008, pp. 287-332.
Baird et al., "Creatine-Kinase- and Exercise-Related Muscle Damage Implications for Muscle Performance and Recovery," Journal of Nutrition and Metabolism, Jan. 11, 2012, Article ID 960363, 13 pages.

Battistelli et al., "Skeletal Muscle Cell Behavior After Physical Agent Treatments," Current Pharmaceutical Design, 2015, 8 pages.
Beaurain, "The Taking in Charge of the Different Officines Recovery Methods in Athleies," The Faculty of Pharmacy of Aix-Marseille University, Apr. 25, 2019, 165 pages.
Beijer et al. "Whole-Body Vibrations Do Not Elevate the Angiogenic Stimulus when Applied during Resistance Exercise," PLOS One, www.plosone.org, Nov. 2013, vol. 8, No. 11, e80143, 11 pages.
Cheung et al., "Delayed Onset Muscle Soreness, Treatment Strategies and Performance Factors," Sports medicine, Feb. 2003, pp. 145-164.
Cisterna et al., "Adapted physical exercise enhances activation and differentiation potential of satellite cells in the skeletal muscle of old mice," Journal of Anatomy, Jan. 6, 2016, pp. 771-783.
Febbraio et al., "Muscle-derived interleukin-6: mechanisms for activation and possible biological roles," FASEB Journal, vol. 16, Sep. 2002, pp. 1335-1347.
Huh et al., "Exercise-Induced Irisin Secretion Is Independent of Age or Fitness Level and Increased Irisin May Directly Modulate Muscle Metabolism Through AMPK Activation," The Journal of Clinical Endocrinology and Metabolism, Nov. 2014, vol. 99, No. 11, pp. E2154-E2161.
Lewis et al., "Muscle Soreness and Delayed-Onset Muscle Soreness," Clinical Sports Medicine, vol. 31, 2012, pp. 255-262.
McAleer et al., "Mechanistic investigation of adult myotube response to exercise and drug treatment in vitro using a multiplexed functional assay system," Articles in PresS. J Appl Physiol, Oct. 9, 2014, 28 pages.
Robson-Ansley et al., "Acute Interleukin-6 Administration Impairs Athletic Performance in Healthy, Trained Male Runners," Rapid Communication, 2004, pp. 411-418.
Shepherd et al., "Resistance training increases skeletal muscle oxidative capacity and net intramuscular triglyceride breakdown in type I and II fibres of sedentary males," Experimental Physiology, 2014, pp. 894-908.
Toraa et al.,"Fatigue of ventilatory muscles, maximal exercise, training," Canadian Society for Exercise Physiology, 2000, pp. 87-101.
Maughan et al., "Characterization of the metabolic effects of irisin on skeletal muscle in vitro," Diabetes, Obesity and Metabolism 2014, 8 pages.

* cited by examiner

METHOD FOR EVALUATING THE ABILITY OF A COMPOSITION TO PREVENT MUSCLE DAMAGE AND FATIGUE; FOOD SUPPLEMENT AND DRUG

The invention relates to an in vitro method of tests aimed at selecting a chemical substance or a chemical composition intended to prevent and/or reduce muscle fatigue and muscle damage induced by physical exertion in human beings.

The subject of the present invention is also abovementioned chemical compositions and food supplements, and medicaments comprising same.

Any period of intense or prolonged muscle activity can cause, in human beings, a decrease in muscle performance considered to be muscle weakness. Muscle weakness can involve all the muscles of the body, and more particularly the skeletal muscles such as, for example, the muscles of the limbs. Depending on its intensity, muscle weakness is characterized by simple "muscle fatigue" or else by a pathological condition linked to a loss of muscle strength, to difficulty in mobilizing the muscles and, in the case of the motor muscles of the limbs, to a difficulty in moving.

By definition, if muscle weakness is reversible in a brief period of time, which can range from a few minutes to a few hours, it is described as muscle fatigue, that is to say, according to the definition of Scherrer and Monod, regarding physical activity "a transient decrease in the working capacity of the muscle, subsequent to muscle activity, occurring for a constant level of prompting of the motor centers reversible by resting [Scherrer et al., "le travail musculaire local et la fatigue chez l'homme" [Local muscle work and fatigue in human beings" ]; J. Physiol. (Paris) 1960; 52:419-501].

On the other hand, when muscle weakness is slow to reverse or difficult to reverse, and associated with structural changes in the muscle, it is considered to be exercise-induced muscle damage (EIMD). Muscle damage causes an immediate weakness of the muscle which can last for several days before disappearing. Furthermore, because of this muscle damage, the muscles involved may swell, become painful and/or rigid for a period of a few days after performing physical exercise that is unusual or excessive for the subject; this phenomenon is called "delayed onset muscle soreness" (DOMS) [Allen D G et al., "Mechanisms of stretch-induced muscle damage in normal and dystrophic muscle: role of ionic changes"; J. Physiol. 2005 Sep. 15; 567(Pt 3): 723-35].

In general, muscle fatigue is considered to be the result of a lack of energy and of key metabolites which allow muscle contractions to respond to the increasing energy demand. After prolonged physical activity, the muscles are fatigued and can no longer contract, even if the nervous system demands that they do so [Baird M F et al., "Creatine-kinase- and exercise-related muscle damage implications for muscle performance and recovery"; J. Nutr. Metab. 2012; Epub 2012 Jan. 11]. There are several biological mechanisms associated with muscle fatigue. The most important are muscle acidosis and ATP depletion due to increased consumption or to a lack of substrates for producing ATP, such as for example glucose, glycogen or blood glucose. Muscle acidosis is the result of the production of lactic acid, which occurs during glycolysis in the absence of oxygen. This lactic acid is rapidly converted into lactate and into hydronium ion. A proportion of the lactate diffuses out of the muscle cell and is found in the blood; this proportion of lactate is called serum lactate. The production of hydronium ions induces a decrease in pH and the occurrence of muscle acidosis, which interferes with the muscle contraction mechanisms.

These mechanisms associated with muscle fatigue can be monitored by numerous biological markers such as, for example, lactate, aqueous ammonia, or oxypurines such as, for example, hypoxanthine and xanthine. Serum lactate is the most well known muscle fatigue biological marker, since an increase in its content in the blood shows that aerobic ATP production is insufficient and needs to be supplemented with anaerobic production thereof.

Furthermore, it has been observed that serum lactate increases as exercise becomes more intense [Finsterer J, "Biomarkers of peripheral muscle fatigue during exercise"; BMC Musculoskelet Disord., 2012; 13:218]. The skeletal muscles when contracting also release myokines, which are cytokines produced by the muscle. Among these myokines, mention may be made of interleukins 6, 8 and 15 (IL-6, IL-8, IL-15), brain-derived neurotrophic factor (BDNF), leukemia inhibitory factory (LIF), fibroblast growth factor (FGF-21 for fibroblast growth factor 21) and follistatin-like protein (FSTL-1 for follistatin-like 1).

Among these myokines, it is known that IL-6 production increases exponentially in response to muscle contractions. It correlates with the duration of the exercise, its intensity, the muscle work involved, and also the endurance capacity of the subject.

During physical exercise, IL-6 appears to act as a hormone in order to mobilize the extracellular substrates or to increase the supply of substrates, such as for example glucose [Finsterer J. "Biomarkers of peripheral muscle fatigue during exercise. BMC Musculoskelet Disord"; 2012; 13:218].

Absent or present in very small amounts in healthy subjects at rest, the IL-6 concentration increases during physical exercise and to very high levels [Febbraio M A et al., "Muscle-derived interleukin-6: mechanisms for activation and possible biological roles"; FASEB J. 2002; 16: 1335-47]. High plasma levels of IL-6 have been associated with an increased feeling of fatigue during physical exercise, resulting in a significant reduction in performance in trained runners [Robson-Ansley P J et al., "Acute interleukin-6 administration impairs athletic performance in healthy, trained male runners"; Can J Appl Physiol. 2004 August; 29(4):411-8].

The IL-6 response to physical exercise is reduced by the consumption of carbohydrates or carbohydrate-rich diets before exercise. It has therefore been proposed that IL-6 acts as a glucose-regulating hormone during physical exercise and is released by the muscles or the liver in order to maintain glycemic homeostasis.

Unusual or vigorous physical exercise can initiate muscle injuries or damage of various intensities (EIMD) as previously defined. The muscle injuries are characterized by structural abnormalities such as disorders at the level of the sarcomeres and membrane damage, inducing the release of cell components, an increase in degradation of muscle proteins and cell permeability, and also inflammatory processes, including the release of cytokines and infiltration by phagocytic cells [Allen D G et al., "Skeletal muscle fatigue: cellular mechanisms"; Physiol Rev. 2008; 88: 287-332; Baird M F et al. J. Nutr. Metab. 2012; Epub 2012 Jan. 11.]. Muscle damage induces a cascade of events resulting in immediate soreness or soreness delayed over time. Muscle soreness refers to the immediate soreness felt by the subject during or just after having performed physical exercise. Muscle soreness is associated with muscle stiffness, with uncomfortable soreness and/or with muscle sensitivity. These symptoms are felt only for a few hours and are relatively transient compared with those of delayed soreness (DOMS) as described previously.

The symptoms thereof are the same as previously described, but their occurrence is delayed by 24 hours after the end of the physical exercise. They are maintained for 72 hours and are relieved slowly within the following 5 to 7 days [Lewis P B et al. "Muscle soreness and delayed-onset muscle soreness" Clin. Sports Med. 2012; 31: 255-62].

Delayed soreness is also considered to be the most common and recurrent form of sports injuries [Cheung K et al., "Delayed onset muscle soreness: treatment strategies and performance factors" Sports Med. 2003; 33: 145-64].

The release of myofiber proteins into the blood can occur at several steps all along the continuum ranging from muscle damage to muscle soreness. The known biological markers of muscle damage are for example creatine kinase and lactate dehydrogenase. Among these markers, creatine kinase is a key enzyme which is released into the bloodstream when muscle damage occurs. Since creatine kinase has the characteristic of being almost exclusively present in muscle tissue, it is commonly assayed in the serum in order to evaluate muscle damage and injuries [Baird M F et al. "Creatine-kinase- and exercise-related muscle damage implications for muscle performance and recovery. J Nutr Metab. 2012; Epub 2012 Jan. 11].

In order to prevent or treat the effects associated with muscle fatigue and with muscle damage, it is necessary to develop effective chemical substances or chemical compositions so as to administer them to the subject likely to produce a physical exertion or to the subject having produced a physical exertion so as to cause the appearance of physical fatigue and of muscle damage.

The administration of such chemical substances or chemical compositions is more particularly carried out orally or parenterally, and even more particularly orally in the form of tablets, gel capsules, granules or soft capsules as food supplements.

The oral administration of such chemical substances or chemical compositions can also take the form of a food composition comprising said chemical substances or chemical compositions.

The development of effective chemical substances or chemical compositions for the prevention and treatment of the effects associated with muscle fatigue and with muscle damage requires a lengthy and expensive research process since it involves an iterative approach between the phases of preparing the substances or compositions and the phases of evaluating the biological performances of said substances or compositions.

In order to improve the productivity of this process, methods for evaluating biological performances that can be used in medium throughput are preferable for screening for and selecting the effective chemical substances and chemical compositions, which involves not carrying out methods of evaluating involving clinical study models, or involving models with biopsies obtained during clinical studies.

Moreover, the methods of biological evaluation using models on animal cells, or involving animals, are less relevant since the metabolism of animals is different than that of human beings.

There is therefore a need to develop a method for selecting a chemical substance or a chemical composition which makes it possible to prevent or reduce muscle fatigue and muscle damage induced by physical exertion in human beings, which is an in vitro method, which is capable of being usable in medium throughput in a screening approach, which does not involve animal cells, which is reproducible, sensitive, discriminating and efficient, in particular by making it possible to concomitantly evaluate the effects of the substances or compositions tested on muscle fatigue and on muscle damage and, finally, which is suitable for the human nutrition market.

For the purposes of the present application, the term "screening" denotes the implementation of techniques aimed at studying, identifying, sorting biologically active molecules. In this approach, only the molecules which have relevant activity according to one or more tests are selected.

The clinical studies in human beings are carried out particularly in sports men and sports women in training phase or in individuals on whom a physical exercise cycle is imposed. These methods are relevant for evaluating the efficacy of a product, but are not accessible for screening and for selecting several ingredients. Beijer et al. have, for example, studied the effect of additional vibrations during a training period of six weeks on the angiogenic response in twenty-six male subjects. The sera were collected in order to assay MMP-2, MMP-9, VEGF and endostatin, which are biological markers for angiogenesis, and also the proliferative capacity of the endothelial cells [Beijer A et al., "Whole-body vibrations do not elevate the angiogenic stimulus when applied during resistance exercise"; PLoS One. 2013 Nov. 15; 8(11): e80143.].

Other literature references refer to clinical studies during which muscle biopsies were taken.

For example, a clinical study was carried out in 13 sedentary subjects in whom oxygen consumption and insulin sensitivity were evaluated before and after an imposed six-week physical training period. Muscle biopsies were taken from eight of them before and after stable-regime pedaling exercise for 60 minutes at an oxygen consumption of approximately 65%.

This study made it possible to analyze the oxidative capacity and the content of intramuscular triglycerides and of perilipins 2 and 5 in the biopsies [Shepherd S O et al., "Resistance training increases skeletal muscle oxidative capacity and net intramuscular triglyceride breakdown in type I and II fibres of sedentary males"; Exp. Physiol. 2014 June; 99(6): 894-908].

Another clinical study studied the physiology of the irisin protein in healthy subjects at various ages and at various levels of physical exercise [Huh J Y et al., "Exercise-induced irisin secretion is independent of age or fitness level and increased irisin may directly modulate muscle metabolism through AMPK activation"; J. Clin. Endocrinol. Metab. 2014 November; 99(11): E2154-61]. Irisin has been proposed as a myokine involved in the effect of exercise on brown adipose tissue. In order to better understand its role, the authors assayed irisin in elderly and young, physically active or sedentary subjects, after physical exercise by a subject on a treadmill. They also performed biopsies in the young, moderately trained subjects before and after an eight-week period of running training. These samples allowed an analysis of the physical exercise-induced gene expression modulations.

Other literature references also refer to study on the effect of physical exercise in animals. Mention may in particular be made of a study regarding the beneficial effect of physical exercise on sarcopenia [Cisterna B et al. "Adapted physical exercise enhances activation and differentiation potential of satellite cells in the skeletal muscle of old mice"; J. Anat. 2016 Jan. 6. doi: 10.1111/joa.12429]. In this context, the amount and the activation of the satellite cells (contributing cells in muscle regeneration), and also their proliferation and differentiation potential, were evaluated in situ in 28-month-old mice subjected to physical exercise on a treadmill. This study made it possible to show that physical exercise is a powerful and non-pharmacological approach for combating sarcopenia and age-related satellite cell deterioration.

Numerous literature references relating to in vitro studies relate to methods used on murine muscle cells, and in particular cells of the C2C12 and L6 murine lines, which are mouse and rat myoblast lines, respectively, capable of rapidly differentiating to form myotubes capable of contracting and of producing muscle proteins.

In this respect, mention may be made of:
- A study relating to the effect of the irisin protein on the metabolism, gene expression and mitochondrial content of C2C12 myocytes [Vaughan R A et al., "Characterization of the metabolic effects of irisin on skeletal muscle in vitro"; Diabetes Obes. Metab. 2014 August; 16(8): 711-8];
- A study relating to the mechanisms of apoptosis, which is essential to skeletal muscle development and homeostasis, on C2C12 myoblasts and myotubes exposed to UV-B radiation, or to hypothermia and hyperthermia, or to a low pH [Battistelli M et al., "Skeletal Muscle Cell Behavior After Physical Agent Treatments"; Curr. Pharm. Des. 2015; 21(25): 3665-72];
- A study relating to the functional response of myotubes, using a method comprising steps of sampling and isolating rat myotubes, followed by a step of treatment with creatine or by a step of electrical stimulation in order to simulate chronic physical exercise [McAleer C W et al., "Mechanistic investigation of adult myotube response to exercise and drug treatment in vitro using a multiplexed functional assay system"; J. Appl. Physiol. (1985). 2014 Dec. 1; 117(11):1398-405];
- A study using a method of evaluation involving cells of the rat L6 muscle line, comprising a step of stimulation of said muscle line, in order to mimic the stress associated with physical exercise, by adding the calcium ionophore A23187; this study made it possible to show a protective effect of polyphenols included in blueberry extracts on the generation of reactive oxygen species, and also on the release of the lactate dehydrogenase and creatine kinase enzymes [Hurst R D et al., "Blueberry fruit polyphenolics suppress oxidative stress-induced skeletal muscle cell damage in vitro"; Mol. Nutr. Food Res. 2010 March; 54(3): 353-63];
- Other literature references relating to in vitro studies relate to methods involving human skeletal muscle cells. In this respect, mention may be made of a study using a method of evaluation involving human skeletal muscle cells taken from the subjects in order to study the consumption of glucose and of fatty acids by adding irisin to the culture medium, and also the induction of expression of genes associated with glucose, glycogen and lipid metabolism on these same irisin-stimulated cultures [Huh J Y et al., "Exercise-induced irisin secretion is independent of age or fitness level and increased irisin may directly modulate muscle metabolism through AMPK activation"; J. Clin. Endocrinol. Metab. 2014 November; 99(11): E2154-61].

It appears that the prior art does not disclose an in vitro method for selecting a chemical substance or a chemical composition which makes it possible to concomitantly prevent muscle fatigue and muscle damage induced by physical exertion in human beings, which is capable of being usable in medium throughput in a screening approach, which does not involve animal cells, which is reproducible, sensitive, discriminating and efficient, and which is suitable for the human nutrition market.

More particularly, the prior art neither discloses nor teaches such methods of selection involving human primary skeleton muscle cells and comprising a step of stimulation by adding an ionophore agent.

Consequently, the absence of suitable and efficient in vitro test methods, which are capable of being suitable in medium throughput, hampers the development of efficient food products or foods which make it possible to concomitantly prevent muscle fatigue and muscle damage induced by physical exertion in human beings.

According to a first aspect, a subject of the invention is a method for evaluating the ability of a chemical substance (S) or of a chemical composition (C) to prevent muscle fatigue and muscle damage induced by physical exertion in human beings, said method being characterized in that it comprises:
- A step a) of culturing human primary skeletal muscle cells;
- A step b) of differentiating the cells obtained in step a) in order to obtain myotubes;
- A step c) of bringing a chemical substance (S) or a chemical composition (C) into contact with the cell medium obtained in step b);
- A step d) of bringing at least one calcium ionophore agent (AI) into contact with the cell medium obtained in step c;
- A step e) of measuring the level of expression of a combination of biological markers comprising or consisting of:
  - At least one biological marker ($M_1$) of glycemic homeostasis, chosen from the elements of the group consisting of the myokines or cytokines produced by muscles,
  - At least one biological marker ($M_2$) of muscle lesions, chosen from creatine kinase and lactate dehydrogenase,
  - At least one biological marker ($M_3$) of ATP metabolism, chosen from the elements of the group consisting of lactate, aqueous ammonia and oxypurines, in the culture medium obtained in step d); and
- A step f) of comparing the levels of expression of each of said three biological markers ($M_1$), ($M_2$) and ($M_3$) measured in step e) with the reference expression level for each of these three biological markers.

The expression "ability to prevent muscle fatigue and muscle damage" is intended to mean, in the context of the present invention, the ability to decrease the period during which a decrease is observed in the performance of the muscles, linked to muscle weakness after carrying out physical exertion and to decrease the intensity of the structural changes in the muscle that can occur after carrying out physical exertion.

In the context of the present invention, the term "physical exertion" is intended to mean the mobilizing and use of one's physical forces for the purposes of overcoming a resistance, and/or achieving a performance, such as performing movements of the body or of one's limbs by means of the contracting of one's muscles.

The term "primary skeleton muscle cell" denotes a cell which is directly extracted from a skeleton muscle.

The term "myotube" denotes a multinuclear cell, formed by the fusion of several myotubes during myogenesis. The myotubes then differentiate into muscle fibers. A myoblast is a stem cell responsible for the formation of skeletal muscles.

For the purposes of the present invention, the term "ionophore agent" is intended to mean an "ion transporter" capable of catalyzing the transport of ions through hydrophobic membranes such as the lipid bilayers of living cells or of vesicles. In particular, a calcium ionophore is capable of enabling calcium ions to enter muscle cells, thus mimicking physical exercise. Among the calcium ionophore agents (AI) used in step d) of the method which is the subject of the present invention, mention may more particularly be made of beauvericin, ionomycin, calcimycin (or A23187) and most particularly calcimycin (or A23187).

For the purposes of the present invention, the term "biological marker" is intended to mean a characteristic which is objectively measured and evaluated as an indicator of normal biological processes, of pathogenic processes, or of pharmacological responses to an external intervention. A biological marker can for example be a substance of which the detection indicates a particular pathological state or, on the contrary, a substance of which the detection indicates a particular physiological state.

The expression "biological marker ($M_1$) of glycemic homeostasis" is intended to a mean a biological marker as previously defined, the variation in expression of which correlates with glycemic homeostasis. Among the biological markers ($M_1$) of glycemic homeostasis of which the level of expression is measured in step e) of the method which is the subject of the present invention, mention may more particularly be made of interleukin-6 (IL-6), interleukin-8 (IL-8), interleukin-15 (IL-15), brain-derived neurotrophic factor (BDNF), leukemia inhibitory factor (LIF) and most particularly interleukin-6, The term "glycemic homeostasis" is intended to mean the ability of an organism to maintain its glycemic equilibrium, regardless of the external stresses, in particular during physical exertion. Glucose moves between its sites of absorption (intestinal mucosa) or of endogenous production (liver) and those of its metabolism intended essentially for producing energy, and in particular the skeletal muscles during physical exertion.

For the purposes of the present application, the IL-6 biological marker comprises the human IL-6 gene (NCBI reference: Gene ID: GenBank: JQ250825.1), and also the products of this gene. In one particular embodiment, the IL-6 biological marker consists of one of the products of the human IL-6 gene. The products of the human IL-6 gene comprise the transcript of the human IL-6 gene and the human IL-6 protein. For the purposes of the present application, the "transcript of the human IL-6 gene" is the polynucleotide of which the sequence has the NCBI reference: GenBank: M54894.1. For the purposes of the present application, the term "human IL-6 protein", is intended to mean the protein of which the peptide sequence is the NCBI reference sequence GenBank: AAD13886.1.

The expression "biological marker ($M_2$) of muscle lesions" denotes a biological marker as previously defined, the variation in expression of which correlates with muscle lesions. Among the biological markers ($M_2$) of muscle lesions, the level of expression of which is measured in step e) of the method which is the subject of the present invention, mention may more particularly be made of creatine kinase and lactate dehydrogenase.

The expression "biological marker ($M_3$) of ATP metabolism" denotes a biological marker as previously defined, the variation in expression of which correlates with ATP metabolism. Among the biological markers ($M_3$) of ATP metabolism, the level of expression of which is measured in step e) of the method which is the subject of the present invention, mention may more particularly be made of lactate, aqueous ammonia and oxypurines.

According to one particular aspect of the method as previously defined, in step e), the biological marker ($M_1$) is interleukin-6, the biological marker ($M_2$) is creatine kinase and the biological marker ($M_3$) is lactate.

For each of the biological markers ($M_1$), ($M_2$) and ($M_3$), the expression "the measurement of the level of expression" refers in general either to a measurement of the amount of transcripts of a gene, or to a measurement of the amount of biological molecules, and more particularly of the proteins and of the metabolites, produced by the human body, or to a level of enzymatic activity.

When the level of expression of the biological marker is measured at the nucleotide level, namely by measuring the amount of products of the gene in its nucleotide form, any method normally used by those skilled in the art for measuring nucleotide amounts can be used, and mention may thus be made of qRT-PCR (quantitative reverse-transcription polymerase chain reaction), DNA chips and in situ hybridization.

When the level of expression of the biological marker is measured at the protein, functional or metabolic level, namely by measuring its amount, whether it is a protein or a metabolite, or by measuring its biological function, any method normally used by those skilled in the art for measuring amounts of protein or of metabolites, or functionalities, can be used and mention may thus be made of ELISA assay, Western blot, mass spectrometry, immunofluorescence, chromatographic techniques and enzymatic activity.

In the method which is the subject of the present invention, the measurement of the expression of the biological marker ($M_1$) of glycemic homeostasis is carried out more particularly at the protein level.

According to one more particular aspect of the method which is the subject of the present invention, when the biological marker ($M_1$) is interleukin-6, the measurement of the interleukin-6 expression is carried out at the protein level and even more particularly with a measurement using a colorimetric ELISA (Enzyme-Linked ImmunoSorbent Assay) method. This method uses an antibody specific for human IL-6, bound to the bottom of the wells of a measuring plate. The samples to be assayed are added to the wells and the IL-6 present in the samples binds to the immobilized antibody. The wells are then washed and another anti-human IL-6 antibody, which is biotinylated, is added.

The wells are once again rinsed in order to remove the non-bound antibody, then streptavidin conjugated to the HRP (horseradish peroxidase) enzyme is added to the wells. The wells are again rinsed and the HRP substrate tetramethylbenzidine is added to the wells. The intensity of the color develops proportionally to the amount of IL-6 bound. The "stop" solution changes the color from blue to yellow, and the color intensity is measured at 450 nm by spectrophotometry. The IL-6 concentration is calculated by referring to a standard range.

In the method which is the subject of the present invention of the method which is the subject of the present invention, the measurement of the expression of the biological marker ($M_2$) of muscle lesions is carried out more particularly at the functional level, and more particularly at the enzymatic activity level.

According to one more particular aspect of the method which is the subject of the present invention, when the biological marker ($M_2$) is creatine kinase, the measurement of the expression of creatine kinase is carried out at the functional level, and even more particularly with a measurement of its enzymatic activity. The enzymatic activity of creatine kinase is determined by colorimetric ELISA method. The assay is based on coupled enzymatic reactions during which creatine phosphate and ADP are converted into creatine and ATP by the creatine kinase present in the sample to be assayed.

The ATP thus produced is then used to phosphorylate glucose in the presence of hexokinase in order to generate glucose 6-phosphate, the latter subsequently being oxidized by NADP in the presence of glucose 6-phosphate dehydrogenase. The amount of NADPH produced at various measurement times, detected at 340 nm, is proportional to the creatine kinase activity of the sample. The creatine kinase activity is then calculated with reference to a calibrated sample.

In the method which is the subject of the present invention, the measurement of the expression of the biological marker ($M_3$) of ATP metabolism is carried out more particularly at the metabolic level.

According to a more particular aspect of the method which is the subject of the present invention, when the biological marker ($M_3$) is lactate, the measurement of the lactate expression is carried out at the metabolic level, and even more particularly with a measurement implementing a colorimetric enzymatic assay.

Briefly, the lactate present in the cell supernatants reacts specifically with an enzymatic mixture to generate a product, which interacts with a specific probe to produce color.

The optical density is measured by spectrophotometry at 570 nm and the lactate concentration is calculated by means of a standard range.

According to an even more particular aspect of the method which is the subject of the present invention, when the biological marker ($M_1$) is interleukin-6, the measurement of the interleukin-6 expression is carried out at the protein level, and even more particularly with a measurement implementing a colorimetric ELISA method, and when the biological marker ($M_2$) is creatine kinase, the measurement of the creatine kinase expression is carried out at the functional level, and even more particularly with a measurement implementing a measurement of its enzymatic activity by colorimetric ELISA method, and when the biological marker ($M_3$) is lactate, the measurement of the lactate expression is carried out at the metabolic level, and even more particularly with a measurement implementing a colorimetric enzymatic assay.

The term "reference expression level" of a biological marker denotes any level of expression of said biological marker used as reference.

For example, a reference expression level can be obtained by measuring the level of expression of said biological marker with a substance known from the prior art for its effect in the prevention of muscle fatigue and muscle damage in human beings, or by measuring the level of expression of said biological marker when the method which is the subject of the present invention is carried out in the absence of step c) and of step d) of said method; the level of expression of the biological marker of interest is then that which corresponds to the culture medium of the non-treated and non-stressed differentiated cells, or by measuring the level of expression of said biological marker when the method which is the subject of the present invention is carried out in the absence of step c) of said method; the level of expression of the biological marker of interest is then that which corresponds to the culture medium of the non-treated and stressed differentiated cells.

In the context of the present invention, a reference expression level of the biological marker ($M_1$) of glycemic homeostasis can be obtained by measuring the level of expression of said biological marker ($M_1$), In the cell culture medium obtained at the end of step b) of the method which is the subject of the invention, without carrying out either step c) or step d) of the method which is the subject of the present invention; this measurement of the level of expression of the marker ($M_1$) on the non-treated and non-stressed differentiated cells is denoted $N^1$, and/or In the cell culture medium obtained after carrying out steps a), b) and d) of the method which is the subject of the present invention, without carrying out step c) of the method which is the subject of the present invention; this measurement of the level of expression of the marker ($M_1$) on the non-treated but stressed differentiated cells is denoted $N^1_0$; and/or In the cell culture medium obtained after carrying out step d) of the method which is the subject of the present invention, when the substance (S) used in step c) of the method which is the subject of the present invention is a substance chosen from the elements of the group consisting of vitamin E, glucose, cyclosporine A, actinomycin D, and more particularly when the substance (S) used in step c) of the method which is the subject of the present invention is vitamin E. This measurement of the level of expression of the biological marker ($M_1$) for a reference substance (S) is denoted $N^1_{Ref}$.

In the context of the present invention, a reference expression level of the biological marker ($M_2$) of muscle lesions can be obtained by measuring the level of expression of said biological marker ($M_2$):

In the cell culture medium obtained at the end of step b) of the method which is the subject of the invention, without carrying out either step c) or step d) of the method which is the subject of the present invention; this measurement of the level of expression on the non-treated and non-stressed differentiated cells is denoted $N^2$, and/or In the cell culture medium obtained after carrying out steps a), b) and d) of the method which is the subject of the present invention, without carrying out step c) of the method which is the subject of the present invention; this measurement of the level of expression on the non-treated but stressed differentiated cells is denoted $N^2_0$, and/or In the cell culture medium obtained after carrying out step d) of the method which is the subject of the present invention, when the substance (S) used in step c) of the method which is the subject of the present invention is a substance chosen from the elements of the group consisting of vitamin E, IL-1 RA (interleukin-1 receptor antagonist), dihydromyricetin, andrographolide and nifedipine and more particularly when the substance (S) used in step c) of the method which is the subject of the present invention is vitamin E. This measurement of the level of expression of the biological marker ($M_2$) for a reference substance (S) is denoted $N^2_{Ref}$.

In the context of the present invention, a reference expression level of the biological marker ($M_3$) of ATP metabolism can be obtained by measuring the level of expression of said biological marker ($M_3$):

In the cell culture medium obtained at the end of step b) of the method which is the subject of the invention, without carrying out either step c) or step d) of the method which is the subject of the present invention; this measurement of the level of expression of the biological marker ($M_3$) on the non-treated and non-stressed differentiated cells is denoted $N^3$, and/or In the cell culture medium obtained after carrying out steps a), b) and d) of the method which is the subject of the present invention, but without carrying out step c) of the method which is the subject of the present invention; this measurement of the level of expression of the biological marker ($M_3$) on the non-treated but stressed differentiated cells is denoted $N^3_0$, and/or In the cell culture medium obtained after carrying out step d) of the method which is the subject of the present invention, when the substance (S) used in step c) of the method which is the subject of the present invention is a substance chosen from the elements of the group consisting of vitamin E, glutathione, magnesium and coenzyme Q10, and more particularly when the substance (S) used in step c) of the method which is the subject of the present invention is vitamin E. This measurement of the level of expression of the biological marker ($M_3$) for a reference substance (S) is denoted $N^3_{Ref}$.

By virtue of the method as previously defined, it is possible to select said substance (S) or said composition (C) as ingredient intended for preventing muscle fatigue and muscle damage induced by physical exertion in human beings, and able to be used as such, or for preparing nutritional supplement compositions comprising same, or for preparing foods comprising same, or for preventing muscle fatigue and muscle damage induced by physical exertion in human beings.

By virtue of the method as previously defined, a substance (S) or a composition (C) will be selected to be used as such, or for preparing nutritional supplement compositions comprising same, or for preparing foods comprising same, for preventing muscle fatigue and muscle damage induced by physical exertion in human beings if:

the level of expression measured for said substance (S) or for said composition (C), denoted $N^1_i$, is greater than the reference expression level of the biological marker ($M_1$) of glycemic homeostasis, and if the level of expression measured for said substance (S) or for said composition (C) denoted $N^2_i$, is greater than the reference expression level of the biological marker ($M_2$) of muscle lesions and the level of expression measured for said substance (S) or for said composition (C), denoted $N^3_i$, is greater than the reference expression level of the biological marker ($M_3$) of ATP metabolism.

A substance (S) or a composition (C) will more particularly be selected to be used as such, or for preparing nutritional supplement compositions comprising same, or for preparing foods comprising same, for preventing muscle fatigue and muscle damage induced by physical exertion in human beings if:

the ratio $R_1 = [(N^1_0 - N^1i) \times 100]/[(N^1_0 - N^1)]$ is greater than $n_1$; if the ratio $R_2 = [(N^2_0 - N^2i) \times 100]/[(N^2_0 - N^2]$ is greater than $n_2$, and if the ratio $R_3 = [(N^3_0 - N^3i) \times 100]/[(N^3_0 - N^3]$ is greater than $n_3$, with:

$n_1$ greater than 20, and more particularly greater than 40,
$n_2$ greater than 20, and more particularly greater than 40 and
$n_3$ greater than 20 and more particularly greater than 40, $N^1$, $N^1_0$, $N^2$, $N^2_0$, $N^3$ and $N^2_0$ being as previously defined.

$n_1$ as defined above is more particularly greater than or equal to 40, most particularly greater than or equal to 70, and even more particularly greater than or equal to 100.

$n_2$ as defined above is more particularly greater than or equal to 40, most particularly greater than or equal to 70, and even more particularly greater than or equal to 100.

$n_3$ as defined above is more particularly greater than or equal to 40, most particularly greater than or equal to 70, and even more particularly greater than or equal to 100.

By virtue of the method as previously defined, a substance (S) or a composition (C) will more particularly be selected $n_1$, $n_2$ and $n_3$ are greater than or equal to 40.

According to another aspect, a subject of the invention is an edible composition ($C_A$) comprising:

at least one salt of a multivalent metal cation ($C_{METAL}$),
at least one compound ($V_E$), chosen from vitamin E or vitamin E acetate,
at least one polyphenolic compound chosen from compounds of the flavanol family, compounds of the anthocyanin family, compounds of the phenolic acid family, and compounds of the family of flavonols and/or of the glucosylated derivatives thereof.

in which the ($C_{METAL}$)/($V_E$) molar ratio is greater than or equal to 0.50 and less than or equal to 2.00, more particularly greater than or equal to 0.50 and less than or equal to 1.50.

A subject of the invention is in particular said composition ($C_A$) as defined above, in which the multivalent metal cation ($C_{METAL}$) is a divalent metal cation, and more particularly a divalent metal cation chosen from calcium, magnesium, zinc, manganese, iron, copper, cobalt, silver, barium, zirconium and strontium cations.

According to one more particular aspect, the multivalent metal cation ($C_{METAL}$) is a divalent metal cation chosen from calcium, magnesium, zinc and strontium.

According to one more particular aspect, the multivalent metal cation ($C_{METAL}$) is the zinc divalent cation.

The multivalent metal cation ($C_{METAL}$) is used in the composition ($C_A$) as previously defined in the form of a salt with an edible organic anion, having at least one carboxylic acid function in carboxylate form, chosen from the elements of the group consisting of the anions derived from glycolic, citric, tartaric, salicylic, lactic, mandelic, ascorbic, pyruvic, fumaric, glycerophosphoric, retinoic, benzoic, kojic, malic, gluconic, galacturonic, propionic, heptanoic, 4-aminobenzoic, cinnamic, benzalmalonic, aspartic and glutamic acids.

According to one particular aspect of the present invention, the multivalent metal cation ($C_{METAL}$) is used in said composition ($C_A$) as previously defined in the form of the gluconate, the glycerophosphate, the aspartate or the glutamate of said multivalent metal cation ($C_{METAL}$).

According to a most particular aspect of the present invention, the multivalent metal cation ($C_{METAL}$) is used in said composition ($C_A$) in the form of the gluconate of said multivalent metal cation ($C_{METAL}$).

The term "vitamin E" denotes, in the definition of said composition ($C_A$) as previously defined:

α-tocopherol or (2R)-2,5,7,8-tetramethyl-2-[(4R,8R)-4,8,12-trimethyltridecyl]-3,4-dihydrochromen-6-ol,
β-tocopherol or (2R)-2,5,8-trimethyl-2-[(4R,8R)-4,8,12-trimethyltridecyl]-3,4-dihydrochromen-6-ol,
γ-tocopherol or (2R)-2,7,8-trimethyl-2-[(4R,8R)-4,8,12-trimethyltridecyl]-3,4-dihydrochromen-6-ol,
δ-tocopherol or (2R)-2,8-dimethyl-2-[(4R,8R)-4,8,12-trimethyltridecyl]-3,4-dihydrochromen-6-ol,
α-tocotrienol or (2R)-2,5,7,8-tetramethyl-2-[(3E,7E)-4,8,12-trimethyltrideca-3,7,11-trienyl]-3,4-dihydrochromen-6-ol, β-tocotrienol or (2R)-2,5,8-trimethyl-2-[(3E,7E)-4,8,12-trimethyltrideca-3,7,11-trienyl]-3,4-dihydrochromen-6-ol, γ-tocotrienol or (2R)-2,7,8-trimethyl-2-[(3E,7E)-4,8,12-trimethyltrideca-3,7,11-trienyl]-3,4-dihydrochromen-6-ol and δ-tocotrienol or (2R)-2,8-dimethyl-2-[(3E,7E)-4,8,12-trimethyltrideca-3,7,11-trienyl]-3,4-dihydrochromen-6-ol.

The terms α-tocopherol, β-tocopherol, γ-tocopherol, δ-tocopherol, α-tocotrienol, β-tocotrienol, γ-tocotrienol and δ-tocotrienol denote either the diastereoisomerically pure forms of each of said compounds as previously stated, or the racemates of said compounds, for instance DL-α-tocopherol.

The acetates of tocopherols, such as α-tocopheryl acetate, β-tocopheryl acetate, γ-tocopheryl acetate or b-tocopheryl acetate, are synthetic compounds obtained from the corresponding tocopherols.

According to one particular aspect, a subject of the invention is said composition ($C_A$) as previously defined, wherein the vitamin E is chosen from the elements of the group consisting of α-tocopherol and α-tocopheryl acetate.

According to a most particular aspect, said composition ($C_A$) as previously defined comprises α-tocopheryl acetate.

The term "compound of the flavanol family" denotes a compound derived from one of the following monomeric structures of formula (I):

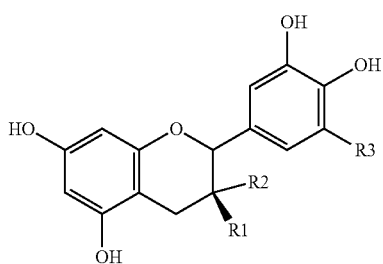

(I)

and in particular:
(+)-catechin when R1=OH, R2=H and R3=H,
(−)-epicatechin when R1=H, R2=OH and R3=H,
(+)-gallocatechin when R1=OH, R2=H and R3=OH, and
(−)-epigallocatechin when R1=H, R2=OH and R3=OH.

The expression "compound of the anthocyanin family" denotes the monoglucosylated or the polyglucosylated compound, including the aglycones (anthocyanidins) having one of the structures of formula (II):

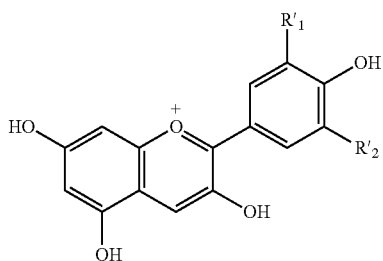

(II)

and in particular:
malvidin when R'1 and R'2 each represent a methoxy radical, peonidin when R'1 represents a methoxy radical and R'2 a hydrogen atom, delphinidin when R'1 and R'2 each represent a hydroxyl radical, and petunidin when R'1 represents a methoxy radical and R'2 a hydroxyl radical.

The expression "compound of the phenolic acid family" denotes more particularly a compound chosen from caftaric, cis-coutaric, trans-coutaric, cafeic, gallic, para-coumaric or 2-S-glutathionylcaftaric acids.

The expression "compound of the family of flavonols or of glucosylated derivatives thereof" denotes more particularly the elements of the group consisting of myricetol glucoside, quercetol glucoside, the compound having one of the structures of formula (III):

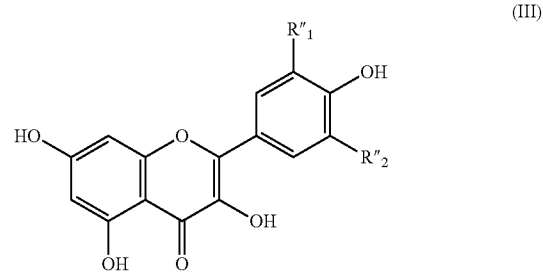

(III)

and in particular:
kaempferol, when R"1 and R"2 each represent a hydrogen atom, quercetin, when R"1 represents a hydroxyl radical and R"2 represents a hydrogen atom, myricetin, when R"1 and R"2 each represent a hydroxyl radical, and isorhametin, when R"1 represents a methoxy radical and R"2 represents a hydrogen atom.

According to one particular aspect, a subject of the invention is said edible composition ($C_A$) as defined above and comprising, for 100% of its weight:

from 5% to 50% by weight, more particularly from 5% to 40% by weight, of a salt of a multivalent metal cation ($C_M$) and of an edible organic anion, from 1% to 35% by weight, more particularly from 5% to 35% by weight and most particularly from 8% to 35% by weight, of at least one compound ($V_E$) chosen from vitamin E or vitamin E acetate, vitamin E acetate, from 0.5% to 80% by weight, more particularly from 1% to 70% by weight of an edible composition (PP) of polyphenolic compounds chosen from compounds of the flavanol family, compounds of the anthocyanin family, compounds of the phenolic acid family, and compounds of the family of flavonols and/or of glucosylated derivatives thereof, from 10% to 93.5% by weight, more particularly from 15% to 89% by weight, of at least one edible processing additive, and wherein the ($C_M$)/($V_E$) molar ratio is greater than or equal to 0.50 and less than or equal to 2.00, more particularly greater than or equal to 0.50 and less than or equal to 1.50.

According to one particular aspect, a subject of the invention is the composition ($C_A$) as defined above, wherein said composition (PP) comprises, for 100% of its weight:

from 60% to 75% by weight of at least one compound of the flavanol family, from 10% to 20% by weight of at least one compound of the anthocyanin family, from 5% to 30% by weight of at least one compound of the phenolic acid family.

According to one most particular aspect, a subject of the invention is the composition ($C_A$) as defined above, wherein said composition (PP) also comprises up to 5% by weight of at least one compound of the family of flavonols or of the glucosylated derivatives thereof.

According to another particular aspect, a subject of the invention is the composition ($C_A$) as defined above, wherein said composition (PP) is an extract of grape juice or of a pulverulent dry residue of red wine and in particular a pulverulent dry residue of red wine obtained by means of a method comprising the following successive steps:

A step a1) of distilling red wine,

A step b1) of concentrating the distillate obtained in step a1), and

A step c1) of drying the concentrate obtained in step b1).

The dry residue of red wine is thus obtained in the form of a powder generally containing at most 5% by weight of moisture.

The term "edible processing additive, present in the composition ($C_A$) which is the subject of the present invention, denotes any chemical substance or any chemical composition of which the technical function is to allow and/or to facilitate the mixing of the various constituents of said composition ($C_A$), to facilitate and/or optimize the physical properties of said composition ($C_A$), for instance to facilitate and/or optimize its flow, its stability and its incorporation into a subsequent pharmaceutical and/or nutritional formulation, and which is capable of adhering to the conditions required by the regulations in force for the marketing of a pharmaceutical formulation and/or of a nutritional formulation.

According to one more particular aspect, at least one edible processing additive present in the composition ($C_A$) which is the subject of the present invention is a diluent, a flow agent, a binder or a disintegrating agent.

Among the diluents that can be combined in the composition ($C_A$) which is the subject of the present invention, mention may be made of lactose, sucrose, saccharose, glucose, maltodextrin, mannitol, sorbitol, xylitol, isomalt, calcium hydrogen phosphate, microcrystalline cellulose, starches and more particularly corn starches, wheat starches, potato starches, dicalcium phosphate, anhydrous dibasic calcium phosphate, sodium carbonate, calcium carbonate and magnesium carbonate, monoglycerides and/or diglycerides of fatty acids comprising from 8 to 24 carbon atoms.

Among the flow agents that can be combined in the composition ($C_A$) which is the subject of the present invention, mention may be made of magnesium stearate, talc, sodium stearyl fumarate, hydrogenated vegetable oils, anhydrous colloidal silica, sodium benzoate and silica dioxide.

Among the binders that can be combined in the composition ($C_A$) which is the subject of the present invention, mention may be made of starches in the form of pastes, pregelatinized starches, hydroxypropylmethylcellulose, methylcellulose, saccharose syrups and acacia gum.

Among the disintegrating agents that can be combined in the composition ($C_A$) which is the subject of the present invention, mention may be made of starches, sodium starch glycolate, alginic acid, sodium alginate, sodium croscarmellose, crospovidone and polyvinylpyrrolidone.

According to one particular aspect, a subject of the invention is said edible composition ($C_A$) as defined above and consisting of, for 100% of its weight:

from 5% to 50% by weight, more particularly from 5% to 40% by weight, of a salt of a multivalent metal cation ($C_M$) and of an edible organic anion, from 1% to 35% by weight, more particularly from 5% to 35% by weight and most particularly from 8% to 35% by weight, of at least one compound ($V_E$), chosen from vitamin E or vitamin E acetate, of vitamin E acetate, from 0.5% to 80% by weight, more particularly from 1% to 70% by weight, of an edible composition (PP) of polyphenolic compounds chosen from compounds of the flavanol family, compounds of the anthocyanin family, compounds of the phenolic acid family, and compounds of the family of flavonols and/or of glucosylated derivatives thereof, from 10% to 93.5% by weight, more particularly from 15% to 89% by weight, of at least one edible processing additive, and wherein the ($C_M$)/($V_E$) molar ratio is greater than or equal to 0.50 and less than or equal to 2.00, more particularly greater than or equal to 0.50 and less than or equal to 1.50.

The composition ($C_A$) which is the subject of the present invention can be in any physical form, and more particularly in the form of a powder.

When the composition ($C_A$) which is the subject of the present invention is in the form of a powder, it is obtained by introducing its various constituents into a mixer equipped with at least one mechanical stirring system, for instance flat stirring blades or impeller-type stirring blades, and the mixer is optionally a tumbler mixer, and the mixer is optionally equipped with a lump breaker system. This mixing operation is generally carried out at ambient temperature.

According to a more particular aspect, a subject of the invention is a composition ($C_A$) which is in the form of a powder and which consists, for 100% of its weight, of:

from 5% to 50% by weight, more particularly from 5% to 40% by weight, of zinc gluconate, from 1% to 35% by weight of α-tocopherol, from 0.5% to 80% by weight of said composition (PP), an edible composition (PP) comprising from 60% to 75% by weight of at least one compound of the flavanol family, from 10% to 20% by weight of at least one compound of the anthocyanin family and from 5% to 30% by weight of at least one compound of the phenolic acid family;

from 10% to 93.5% by weight, more particularly from 15% to 89% by weight, of at least one edible processing additive, and wherein the ($C_M$)/($V_E$) molar ratio is greater than or equal to 0.50 and less than or equal to 2.00, more particularly greater than or equal to 0.50 and less than or equal to 1.50.

The evaluation of the composition ($C_A$) as previously defined, by means of the method which is the subject of the present invention, reveals that all three of the ratios $R_1$, $R_2$ and $R_3$, as previously defined, are greater than 40.

According to another aspect, a subject of the invention is the use of the composition ($C_A$) as previously defined, for preparing a food supplement composition, and also the use thereof as a food supplement.

For the purposes of the present application, the term "food supplement composition", is intended to mean a composition, the purpose of which is to provide a supplement of nutrients or of substances having a nutritional or physiological effect, which are lacking or in insufficient amount in the normal diet of an individual.

A food supplement composition constitutes a concentrated source of nutrients or of other substances having a nutritional or physiological effect, alone or in combination, and makes it possible to prevent certain deficiencies or to meet specific needs in the diet of an individual, in particular during physical exertion.

The food supplement compositions also satisfy the definition as presented in Article 2 of Decree No. 2006-352 of Mar. 26, 2006, of the French Republic relating to food supplements and/or of Directive 2002/46/EC of the European Parliament and of the Counsel of Jun. 10, 2002.

For the purposes of the present application, the term "food composition" is intended to mean a composition comprising foods, namely any transformed, partially transformed or non-transformed substance or product intended to be ingested or reasonably likely to be ingested by human beings. The foods also correspond to the definition present in European Regulation 178/2002/EC.

According to another aspect, a subject of the invention is a food supplement composition characterized in that it comprises, for 100% of its weight, from 5% to 70% by weight, more particularly from 10% to 70% by weight, and even more particularly from 25% to 70% by weight, of the composition ($C_A$) as previously defined.

According to one particular aspect, the food supplement composition which is the subject of the present invention is in any presentation form known to those skilled in the art, for instance in the form of a tablet, a gel capsule, a soft capsule, a syrup, a powder, for instance an immediate-release powder, a delayed-release powder or a powder for reconstituted drinks, a liquid, a stick or a gel.

According to another aspect, a subject of the invention is a food composition characterized in that it comprises, for 100% of its weight, from 5% to 70% by weight, more particularly from 10% to 70% by weight, and even more particularly from 25% to 70% by weight, of the composition ($C_A$) as previously defined.

According to one particular aspect, the food composition which is the subject of the present invention is in any food product form known to those skilled in the art, such as a drink, and more particularly an aqueous drink, a solution, a fruit juice, a flavored drink, an energy drink, an alcoholic drink, a coffee-based drink, a chocolate-based drink, a tea-based drink, a milk product, and more particularly milk, yoghurt, a milk desert, drinkable yoghurt, a cheese, an ice cream, a chocolate bar, a cereal product, and more particularly a cereal bar, a cookie, breakfast cereal, flours, breadmaking products, a specialized nutrition product, more particularly an infant nutrition product, a nutrition product to prepare for physical exertion, a clinical nutrition product, a meal substitute, candies, more particularly chewing gums, sweets, caramels, dragees, lozenges, marshmallows, turkish delight, nougats, fruit jellies, liquorice.

In general, the food supplement composition which is the subject of the present invention can also comprise active ingredients normally used in the nutrition field, such as bioactive lipids, water-soluble or water-dispersible trace element salts, water-soluble or fat-soluble vitamins, prebiotics, probiotics, milk proteins and/or protein concentrates, plant or animal enzymes, amino acids, peptides, sugars, taste enhancers, flavoring agents.

As bioactive lipids optionally present in the food supplement composition which is the subject of the present invention, mention may be made of phytosterols, such as those extracted from vegetable oils, and more particularly extracts of sea buckthorn oil, of corn oil, of soybean oil; phytosterol complexes isolated from vegetable oils, for instance cholestatin, composed of campesterol, of stigmasterol and of brassicasterol; phytostanols; carotenoids, which belong to the family of terpenoids, extracted from algae, green plants, fungi, bacteria; polyunsaturated fatty acids of the omega-3 group, for instance alpha-linolenic acid, eicosapentaenoic acid, docosahexanoic acid; polyunsaturated fatty acids of the omega-6 group, for example linoleic acid, γ-linolenic acid, eicosadienoic acid, dihomo-γ-linolenic acid, arachidonic acid, docosadienoic acid, docosatetraenoic acid, docosapentaenoic acid.

As examples of water-soluble or water-dispersible trace element salts optionally present in the food supplement composition which is the subject of the present invention, mention may be made of ferrous carbonate, ferrous chloride tetrahydrate, ferric chloride hexahydrate, ferrous citrate hexahydrate, ferrous fumarate, ferrous lactate tetrahydrate, ferrous sulfate monohydrate, ferrous sulfate heptahydrate, ferrous chelate of amino acid hydrates, glycine iron chelate; calcium iodate hexahydrate, anhydrous calcium iodate; sodium iodide, potassium iodide; cobalt acetate tetrahydrate, basic cobalt carbonate monohydrate, cobalt carbonate hexahydrate, cobalt sulfate heptahydrate, cobalt sulfate monohydrate, cobalt nitrate hexahydrate; cupric acetate monohydrate, basic copper carbonate monohydrate, cupric chloride dihydrate, copper methionate, cupric sulfate pentahydrate, cuprous chelate of amino acid hydrates, cuprous chelate of hydrated glycine, cuprous chelate of methionine hydroxy analog; manganous carbonate, manganous chloride tetrahydrate, manganese acid phosphate trihydrate, manganous sulfate tetrahydrate, manganous sulfate monohydrate, manganous chelate of amino acid hydrate, manganous chelate of glycine hydrate, manganous chelate of methionine hydroxy analog; ammonium molybdate, sodium molybdate, sodium selenite, sodium selenate; the organic form of selenium produced by *Saccharomyces cerevisiae*, selenomethionine (inactivated selenium yeast), and selenomethionine produced by *Saccharomyces cerevisiae* (inactivated selenium yeast).

As examples of water-soluble or fat-soluble vitamins optionally present in the food supplement composition which is the subject of the present invention, mention may be made of: vitamin A, more particularly in the retinol, retinyl acetate, retinyl palmitate or beta-carotene form thereof; vitamin D2, more particularly in the ergocalciferol, or 25-hydroxcalciferol, form thereof, vitamin D3, more particularly in the cholecalciferol form thereof, vitamin K, more particularly in the phylloquinone (phytomenadione) or menaquinone form thereof, vitamin B1, more particularly in the thiamine hydrochloride, thiamine mononitrate, thiamine chloride monophosphate or thiamine chloride pyrophosphate form thereof, vitamin B2, more particularly in the riboflavin, or riboflavin 5'-phosphate sodium, form thereof, vitamin B6, more particularly in the pyridoxine hydrochloride, pyridoxine 5'-phosphate or pyridoxal 5'-phosphate form thereof, vitamin B12, more particularly in the cyanocobalamin, hydroxocobalamin, 5'-deoxyadenosylcobalamin or methylcobalamin form thereof, vitamin C, more particularly in the L-ascorbic acid, sodium L-ascorbate, calcium L-ascorbate, potassium L-ascorbate, palmityl-6-L-ascorbic acid calcium salt, sodium ascorbyl monophosphate or pantothenic acid form thereof, more particularly in the calcium D-pantothenate, sodium D-pantothenate, dexpanthenol or pantethine form thereof, vitamin PP, more particularly in the nicotinic acid, niacin, nicotinamide or inositol hexanicotinate in the folic acid form thereof or in the folate form thereof, said folates more particularly being in their pteroylmonoglutamic acid form, calcium L-methylfolate form or (6S)-5-rethyltetrahydrofolic acid form in the form of glucosamine salt, vitamin H2, B7 or BW, more particularly in the biotin form thereof or the choline form thereof, more particularly in the choline chloride, choline dihydrogen citrate or choline bitartrate form thereof, inositol, carnitine, more particularly in the L-carnitine or L-carnitine-L-tartrate form thereof, and taurine.

As examples of prebiotics optionally present in the food supplement composition which is the subject of the present invention, mention may be made of inulin, trans-galactooligosaccharides, fructans and mannooligosaccharides.

As examples of probiotics optionally present in the food supplement composition which is the subject of the present invention, mention may be made of various strains of *Saccharomyces cerevisiae*, of *Bacillus cereus* var *toyoi*, of *Bacillus subtilis* alone or in combination with *Bacillus licheniformis*, or strains of *Enteroccocus faecium*.

These microorganism strains are generally linked to a solid support, for example calcium carbonate, dextrose or sorbitol.

As examples of proteins and/or protein concentrates optionally present in the food supplement composition which is the subject of the present invention, mention may be made of milk proteins resulting from the cracking of milk, such as colostrum in the form of freeze-dried or spray-dried powder, whey in the form of powder, of purified fractions or of fractions enriched in IgG, in lactoferrin, in lactoperoxydase.

As examples of plant or animal enzymes optionally present in the food supplement composition which is the subject of the present invention, mention may be made of promutase, superoxide dismutase (SOD), 3-phytase, 6-phytase, endo-1,4-betaglucanases, endo-1,4-betaxylanases, or else other enzymes which improve or promote digestion.

As examples of peptides optionally present in the food supplement composition which is the subject of the present invention, mention may be made of avocado peptides, lupin peptides, *quinoa* peptides, maca peptides, fermented or non-fermented soy peptides, rice peptides, the peptides present in acacia *macrostachya* seed extract, the peptides present in passionflower seed extracts.

As example of amino acids optionally present in the food supplement composition which is the subject of the present invention, mention may be made of alanine, arginine, asparagine, aspartic acid, cysteine, glutamic acid, glutamine, glycine, histidine, isoleucine, leucine, lysine, methionine, phenylalanine, proline, hydroxyproline, pyrrolysine, selenocysteine, serine, threonine, tryptophan, tyrosine, valine, sarcosine and ornithine.

As examples of sugars optionally present in the food supplement composition which is the subject of the present invention, mention may be made of water-soluble polysaccharides, low-molecular-weight sugars, such as oligosaccharides, monosaccharides or disaccharides, for instance glucose, lactose or dextrose.

As examples of taste enhancers optionally present in the food supplement composition which is the subject of the present invention, mention may be made of glutamates, for instance glutamic acid, monosodium glutamate, monopotassium glutamate, calcium diglutamate, ammonium glutamate or magnesium diglutamate; guanylates, for instance guanylic acid (guanosinemonophosphate), disodium guanylate, dipotassium guanylate or calcium guanylate; inosinates, for instance inosinic acid, disodium inosinate, dipotassium inosinate or calcium inosinate, or else intense sweeteners such as *Stevia* extracts or rebiaudosides.

According to another aspect, a subject of the invention is the edible composition ($C_A$), as previously defined, for carrying out a method for the treatment of the human body by therapy and more particularly for use thereof for preventing muscle fatigue and/or muscle damage induced by physical exertion, in a method for the treatment of the human body by therapy.

The following experimental summary illustrates the invention without however limiting it.

A-1)—Choice of Cells and Time Course

A-1-1)—Culture Step

The cells retained for carrying out the method which is the subject of the present invention are human primary skeletal muscle cells from the gluteus maximus muscle (in the case of muscle exertion in human beings), and because of their ability to differentiate into myotubes (or muscle fibers).

In order to evaluate their differentiation capacity, the cells were cultured in 48-well plates at 10 000 cells/well, in a specific culture medium, at 37° C. in a humid atmosphere containing 5% of $CO_2$. Each condition is carried out in quadruplicate.

A-1-2)—Differentiation Step

When the cells reached 70% to 80% confluence, their culture medium was replaced with differentiation medium, so as to obtain myotubes. The differentiation of the myoblasts into myotubes was evaluated by measuring the intracellular creatine kinase activity at the end of several durations, so as to determine the optimal duration of the differentiation step. The intracellular creatine kinase activity is measured with an assay kit by spectrophotometric measurement at 340 nm at different times. The results obtained are expressed in mU/mg of proteins.

The results obtained showed an optimal creatine kinase activity after a period of 10 days of differentiation, and showed that this creatine kinase activity is greater for a cell passage R3 than for a cell passage R4.

The differentiation step of the method according to the invention is therefore carried out for a period of 10 days for a cell passage R3.

A-1-3)—Differentiated-Cell Stress Step

Several concentrations of the ionophore agent calcimycin (or A23187) were tested on the differentiated cells obtained in the previous step.

For each of these concentrations, the amount of lactate, the amount of interleukin IL-6 and the level of activity of the creatine kinase (CK) were evaluated.

The measurement of the amount of lactate and of the amount of interleukin IL-6 was carried out by recovering the supernatants from each culture medium.

The lactate was quantified with an assay kit by spectrophotometric measurement at 575 nm, compared with a standard range of lactate. The results were expressed in pg/µg of DNA.

The IL-6 was quantified with an assay kit by spectrophotometric measurement at 450 nm, compared with a standard range of IL-6. The results were expressed in pg/µg of DNA.

The cell layers were lyzed in PBS buffer using a sonication probe and two evaluations were carried out on said cells layers:
- An evaluation of the creatine kinase (CK) activity with an assay kit by spectrophotometric measurement at 340 nm at different times. The results were expressed in mU/µg of DNA; and
- An evaluation of the amount of DNA by fluorimetric assay using a DNA intercalating agent, the Hoescht reagent, compared with a standard range of DNA.

The results of the amount of lactate and of IL-6 and the results of the creatine kinase (CK) activity were expressed relative to the amount of DNA present in the layers.

A statistical analysis by means of the Student's test was carried out in order to compare the amounts of lactate and of IL-6 measured, and the creatine kinase (CK) activity measured for each calcimycin (or A23187) concentration tested and for differentiated cells obtained in the previous step, not combined with calcimycin (or A23187).

The results obtained made it possible to show that the optimal calcimycin (or A23187) concentration is 1 µmol/liter (or 1 µM).

A-2)—Definition of the Optimal Method.

The method therefore comprises the following steps:
- Step a) of culturing human primary skeletal muscle cells from the gluteus maximus muscle according to the operating conditions described in section A-1-1) above,
- Step b) of cell differentiation of the medium obtained in step a) according to the operating conditions described in section A-1-2) above, and in particular for a period of 10 days for a cell passage R3,
- Step c) of bringing the culture medium obtained in step b) into contact with the substance or the composition to be tested,
- Step d) of bringing the medium obtained in step c) into contact with calcimycin (or A23187) at a concentration of 1 µmol/liter (or 1 µM),
- Step e) of measuring the amount of lactate and the amount of interleukin IL-6, on the culture medium supernatant, and of measuring the creatine kinase (CK) activity according to the methods described in section A-1-3) above,
- Step f) of comparing the levels of expression of creatine kinase (CK), of IL-6 and of lactate. More specifically, in the context of this step f) the following are calculated:

The ratio $R_1=[(N^1_0-N^1i)\times 100]/[(N^1_0-N^1)]$ for the extracellular interleukin IL-6 with:

$N^1$ corresponding to the amount of IL-6 measured in the culture medium obtained at the end of the method as described above, without carrying out either step c) or step d) of the method (non-treated and non-stressed differentiated cells), $N^1_0$ corresponding to the amount of IL-6 measured in the culture medium obtained at the end of the method as described above, without carrying out step c) of the method (non-treated but stressed differentiated cells), $N^1i$ corresponding to the amount of IL-6 measured in the culture medium obtained at the end of the method as described above, when a substance or a composition (i) is used in step c) of the method (treated and stressed differentiated cells);

The ratio $R_2=[(N^2_0-N^2i)\times 100]/[(N^2_0-N^2)]$ for the intracellular creatine kinase with:

$N^2$ corresponding to the creatine kinase activity measured in the culture medium obtained at the end of the method as described above, without carrying out either step c) or step d) of the method (non-treated and non-stressed differentiated cells), $N^2_0$ corresponding to the creatine kinase activity measured in the culture medium obtained at the end of the method as described above, without carrying out step c) of the method (non-treated but stressed differentiated cells), $N^2i$ corresponding to the creatine kinase activity measured in the culture medium obtained at the end of the method as described above, when a substance or a composition (i) is used in step c) of the method (treated and stressed differentiated cells);

The ratio $R_3=[(N^3_0-N^3i)\times 100]/[(N^3_0-N^3)]$ for the extracellular lactate with:

$N^3$ corresponding to the amount of lactate measured in the culture medium obtained at the end of the method as described above, without carrying out either step c) or step d) of the method (non-treated and non-stressed differentiated cells), $N^3_0$ corresponding to the amount of lactate measured in the culture medium obtained at the end of the method as described above, without carrying out step c) of the method (non-treated but stressed differentiated cells), $N^3i$ corresponding to the amount of lactate measured in the culture medium obtained at the end of the method as described above, when a substance or a composition (i) is used in step c) of the method (treated and stressed differentiated cells).

B]—Evaluation of Substances and of Compositions According to the Method which is the Subject of the Present Invention.

The composition ($C_1$) was prepared by mixing its various constituent ingredients by successively introducing its constituent ingredients into a mixer equipped with a mechanical stirrer system equipped with flat stirrer blades or impeller-type blades, at a temperature of 25° C.

The composition $C_1$ consists, for 100% of its weight, of:
- 38.2% of zinc gluconate,
- 31.0% by weight of D-α tocopheryl acetate,
- 23.18% by weight of corn starch,
- 6.02% by weight of silica dioxide,
- 1.6% by weight of a dry residue of red wine, sold under the name Provinol™, and comprising a polyphenolic acid content of 90% by weight.

The results obtained by carrying out the method of evaluation which is the subject of the present patent application are set out in Table 1 below:

TABLE 1

| Product tested (% by weight) | Extracellular IL-6 (pg/µg of DNA) | Intracellular creatine kinase activity (pg/µg of DNA) | Extracellular lactate (pg/µg of DNA) |
|---|---|---|---|
| Non-treated and non-stressed differentiated cells | $N^1 = 3.95 \pm 1.56$ | $N^2 = 38.07 \pm 5.36$ | $N^3 = 14.62 \pm 1.87$ |
| Non-treated and stressed differentiated cells | $N^1_0 = 12.29 \pm 1.43$ | $N^2_0 = 16.86 \pm 8.04$ | $N^3_0 = 24.92 \pm 4.77$ |
| Differentiated cells treated with Provinol ™(*) (0.00005%) and stressed | $N^1_i = 11.47 \pm 1.42$  $R_1 = 10$ | $N^2_i = 12.66 \pm 2.16$  $R_2 = -20$ | $N^3_i = 25.13 \pm 1.74$  $R_3 = -2$ |

TABLE 1-continued

| Product tested (% by weight) | Extracellular IL-6 (pg/μg of DNA) | Intracellular creatine kinase activity (pg/μg of DNA) | Extracellular lactate (pg/μg of DNA) |
|---|---|---|---|
| Differentiated cells treated with GlnZn(**) (0.00015% of Zn) and stressed | $N^1_i = 12.44 \pm 1.80$<br>$R_1 = -2$ | $N^2_i = 10.73 \pm 2.28$<br>$R_2 = -29$ | $N^3_i = 28.33 \pm 6.43$<br>$R_3 = -33$ |
| Differentiated cells treated with vitamin E(***) (0.001%) and stressed | $N^1_i = 16.55 \pm 5.99$<br>$R_1 = -51$ | $N^2_i = 26.88 \pm 2.82$<br>$R_2 = 47$ | $N^3_i = 27.34 \pm 3.43$<br>$R_3 = -24$ |
| Differentiated cells treated with ($C_1$) (0.001%) and stressed | $N^1_i = 7.00 \pm 0.72$<br>$R_1 = 63$ | $N^2_i = 33.24 \pm 9.35$<br>$R_2 = 77$ | $N^3_i = 16.12 \pm 4.59$<br>$R_3 = 85$ |

(*)Provinol™ is a dry residue of red wine, comprising a polyphenolic compound content of 90% by weight for 100% of its weight, i.e. a weight proportion of polyphenolic compounds of 1.44%.
(**)the zinc gluconate comprises a zinc divalent cation content of 12.2%
(***)the vitamin E is D-α tocopheryl acetate Analysis of the Results The ratios $R_1$, $R_2$ and $R_3$ are below 40, for the cells treated with Provinol™ (dry residue of red wine based on polyphenolic compounds). The same is true for the cells treated with zinc gluconate. It is deduced from this that neither Porvinol™ nor zinc gluconate and, consequently, the zinc divalent cation, can be selected alone for preventing muscle fatigue and muscle damage induced by physical exertion in human beings.

The ratios $R_1$ and $R_3$ are below 40, and the ratio $R_2$ is above 40 ($R_2$=47), for the cells treated with D-α-tocopheryl acetate. This product therefore cannot also be selected for preventing muscle fatigue and muscle damage induced by physical exertion in human beings.

Conversely, the ratios $R_1$, $R_2$ and $R_3$ are all above 40 for cells treated with the composition ($C_1$).

This composition ($C_1$) can be selected for preventing muscle fatigue and muscle damage induced by physical exertion in human beings.

The invention claimed is:

1. An edible composition ($C_A$) consisting essentially of:
   zinc gluconate comprising a zinc divalent cation ($C_{METAL}$),
   at least one compound ($V_E$), chosen from vitamin E or vitamin E acetate,
   at least one edible composition (PP) of polyphenolic compounds chosen from compounds of the flavanol family, compounds of the anthocyanin family, compounds of the phenolic acid family, and compounds of the family of flavonols and/or glucosylated derivatives of compounds of the family of flavonols,
   wherein the ($C_{METAL}$)/($V_E$) molar ratio is greater than or equal to 0.50 and less than or equal to 1.50.

2. The composition (CA) as defined in claim 1, comprising, for 100% of its weight:
   From 5% to 50% by weight of the zinc gluconate,
   From 1% to 35% by weight of the at least one compound ($V_E$),
   From 0.5% to 80% by weight of the at least one edible composition (PP) of polyphenolic compounds,
   From 10% to 93.5% by weight of at least one pharmaceutically and/or nutritionally acceptable processing additive.

3. A food supplement composition comprising a tablet, a gel capsule, a soft capsule, a syrup, a powder, an immediate-release powder, a delayed-release powder, a powder for reconstituted drinks, a liquid, a stick, or a gel comprising the edible composition ($C_A$) as defined in claim 1.

4. A food supplement comprising a tablet, a gel capsule, a soft capsule, a syrup, a powder, an immediate-release powder, a delayed-release powder, a powder for reconstituted drinks, a liquid, a stick, or a gel comprising the edible composition ($C_A$) as defined in claim 2.

5. An edible composition ($C_A$) comprising:
   zinc gluconate comprising a zinc divalent cation ($C_{METAL}$),
   at least one compound ($V_E$), chosen from vitamin E or vitamin E acetate,
   at least one edible composition (PP) of polyphenolic compounds chosen from compounds of the anthocyanin family, compounds of the phenolic acid family, and compounds of the flavanol family and/or glucosylated derivatives of compounds of the flavanol family,
   wherein the ($C_{METAL}$)/($V_E$) molar ratio is greater than or equal to 0.50 and less than or equal to 1.50, and wherein the composition comprises for 100% of its weight:
   from 5% to 40% by weight of the zinc gluconate,
   from 8% to 35% by weight of the at least one compound ($V_E$),
   from 1% to 70% by weight of the at least one edible composition (PP) of polyphenolic compounds,
   from 15% to 89% by weight of at least one pharmaceutically and/or nutritionally acceptable diluent, flow agent, binder, or disintegrating agent.

* * * * *